(12) United States Patent
Rafler et al.

(10) Patent No.: US 8,431,678 B2
(45) Date of Patent: Apr. 30, 2013

(54) METHOD FOR PRODUCING CYCLIC DIESTERS OF L-, D- AND D,L-LACTIC ACID

(75) Inventors: Gerald Rafler, Potsdam (DE); Jutta Rafler, Potsdam (DE); Andreas Windsperger, Maria Anzbach (AT); Robert Edlauer, Laa a.d. Thaya (AT); Josef Gass, Drösing (AT)

(73) Assignee: Jungbunzlauer Austria AG, Vienna (AT)

( * ) Notice: Subject to any disclaimer, the term of this patent is extended or adjusted under 35 U.S.C. 154(b) by 289 days.

(21) Appl. No.: 12/742,361

(22) PCT Filed: Nov. 14, 2008

(86) PCT No.: PCT/AT2008/000413
§ 371 (c)(1),
(2), (4) Date: Aug. 31, 2010

(87) PCT Pub. No.: WO2009/062224
PCT Pub. Date: May 22, 2009

(65) Prior Publication Data
US 2010/0331512 A1 Dec. 30, 2010

(30) Foreign Application Priority Data
Nov. 14, 2007 (AT) .................. A 1838/2007

(51) Int. Cl.
*C08G 63/08* (2006.01)
(52) U.S. Cl.
USPC ................ 528/354; 528/357; 549/274
(58) Field of Classification Search .......... 528/354, 528/357; 549/274
See application file for complete search history.

(56) References Cited

U.S. PATENT DOCUMENTS

| | | | |
|---|---|---|---|
| 4,996,385 A | 2/1991 | Cullo et al. | 585/640 |
| 5,053,522 A | 10/1991 | Muller | 549/274 |
| 5,194,473 A | 3/1993 | Shinoda et al. | 524/263 |
| 5,357,034 A * | 10/1994 | Fridman et al. | 528/354 |
| 5,357,035 A | 10/1994 | Gruber et al. | 528/354 |
| 5,403,897 A | 4/1995 | Ebato et al. | 525/444 |
| 5,605,981 A | 2/1997 | Imamura et al. | 525/440 |
| 5,616,657 A | 4/1997 | Imamura et al. | 525/437 |
| 5,770,682 A | 6/1998 | Ohara et al. | 528/354 |
| 5,844,066 A | 12/1998 | Kakizawa | 528/354 |
| 5,866,677 A | 2/1999 | Maeda et al. | 528/354 |
| 6,005,067 A | 12/1999 | Gruber et al. | 528/354 |
| 6,166,169 A | 12/2000 | Fritz et al. | 528/272 |
| 6,277,951 B1 | 8/2001 | Gruber et al. | 528/354 |
| 6,291,597 B1 | 9/2001 | Gruber et al. | 525/450 |
| 6,326,459 B1 | 12/2001 | Delaite et al. | 528/357 |
| 6,417,320 B1 | 7/2002 | Otto et al. | 528/279 |
| 6,489,508 B1 | 12/2002 | Van Gansbeghe et al. | 562/589 |
| 6,657,042 B2 * | 12/2003 | Rafier et al. | 528/357 |
| 6,875,839 B2 | 4/2005 | Gerking et al. | 528/354 |
| 7,049,376 B2 * | 5/2006 | Duan | 526/89 |
| 2003/0060595 A1* | 3/2003 | Rafler et al. | 528/272 |
| 2004/0014991 A1 | 1/2004 | Van Gansberghe et al. | 549/274 |
| 2005/0165206 A1 | 7/2005 | Rafler et al. | 528/272 |

FOREIGN PATENT DOCUMENTS

| | | |
|---|---|---|
| CN | 1651479 | 8/2005 |
| EP | 0 261 572 | 9/1987 |
| EP | 1 043 066 | 10/2000 |
| GB | 2 407 572 | 6/2006 |
| JP | 7206851 | 8/1995 |
| JP | 08-193123 | 7/1996 |
| WO | WO 93/15127 | 8/1993 |
| WO | WO 94/07949 | 4/1994 |
| WO | WO 94/08078 | 4/1994 |
| WO | WO 98/36008 | 8/1998 |
| WO | WO 99/43669 | 9/1999 |
| WO | WO 01/81610 | 11/2001 |

OTHER PUBLICATIONS

Auras, et al., "An Overview of Polylactides as Packaging Materials", *Macromol. Biosci.* 2004, 4, 835-864.
Drumright, et al., "Polylactic Acid Technology", *Adv. Mater.* 2000, 12, No. 23, Dec. 1.
Grijpma, et al., "(Co)polymers of l-lactide, $2^{a}$", *Macromol. Chem. Phys.* 195, 1649-1663 (1994).
Kricheldorf, et al. "Anionic and Pseudoanionic Polymerization of Lactones—A Comparison", *Makromol. Chem., Macromol. Symp.* 32, 285-298 (1990).
Perego, et al., "Effect of Molecular Weight and Crystallinity on Poly(lactic acid) Mechanical Properties", *Journal of Applied Polymer Science*, vol. 59, 37-43 (1996).
Schmack, et al., "Biodegradable Fibers of Poly(L-lactide) Produced by High-Speed Melt Spinning and Spin Drawing", *Journal of Applied Polymer Science*, vol. 73, 2785-2797 (1999).
DuPont Tyzor Organic Titanates and Zirconates, A Broad Line of Versatile, High-Quality Solutions for Enhancing Your Products' Performance, 2008.
DuPont Tyzor Organic Titanates Product Information—Tyzor LA, 2001.
Kricheldorf, "Tin-Initiated Polymerizations of Lactones: Mechanistic and Preparative Aspects", *Macromol. Symp.* 153, 55-65 (2000).
Kricheldorf, "Syntheses and application of polylactides", *Chemosphere* 43 (2001) 49-54.
Rafler, et al., "Technologically Relevant Aspects of Kinetics and Mechanism of Ring-Opening Polymerization of L,L-Dilactide", *Macromol. Mater. Eng.* 2001, 286, 761-768.
Rafler, et al., "Zur Katalyse der Polyesterbildung durch Metallalkoxide" *Acta Polymerica* 39 (1988) Nr. 4. (abstract in English).
Office action dated Sep. 27, 2012 for U.S. Appl. No. 12/742,185.

* cited by examiner

*Primary Examiner* — Gregory Listvoyb
(74) *Attorney, Agent, or Firm* — Drinker Biddle & Reath LLP

(57) ABSTRACT

Method for the production of L,L-, D,D-, D,L- and meso-dilactides, comprising the polycondensation and/or polytransesterification of an L-, D- or D,L-lactic acid or of esters thereof to polyesters of higher molecular weights of the L-, D- and D,L-lactic acid (polylactic acids) and cyclizing depolymerization of the polylactic acids to dilactides, wherein the polyesters of higher molecular weights of the L-, D- and D,L-lactic acids are produced in the presence of hydrolysis-stable metal compounds as catalyst.

6 Claims, No Drawings

METHOD FOR PRODUCING CYCLIC DIESTERS OF L-, D- AND D,L-LACTIC ACID

The present invention relates to a method for the efficient production of dilactides of high chemical and/or optical purity by selective catalysis of the polycondensation of lactic acid to polylactic acid followed by cyclizing depolymerization of the polyester to a cyclic dimer.

STATE OF THE ART

International developments on the plastic market show that a poly-L-lactic acid (PLA) has the best prospects on the market for alternative plastics because of its typically thermoplastic character, the possibility of use-specific adaptation of the material properties by compounding and chemical modification typical for thermoplastics and especially heterochain polymers, its biogenic raw material base, and the biodegradability of the polymer. It is not only obvious that there is a vast market with strong growth potential for this polymeric material in application areas that require only temporary stability and where recyclability is difficult, such as with

- hygienic materials (baby diapers, incontinence products),
- selected packaging means, especially dishes for fruit, meat and sausage products as well as fish,
- diverse medical products with one-way character,
- sheets for agriculture and forestry as well as plant containers, but also that PLAs have realistic prospects to become a substitute for conventional polyester materials in synthetic fiber materials used for high-quality functional clothing (sports, leisure wear) as well as polymer granulates for injection molding and extrusion molding for obtaining molded articles with long-term stability. In addition, PLA-based biomaterials for surgical and galenic uses are an attractive future market in the sector of high-tech medical products with high prices.

This extended application profile of PLA plastics requires high-purity starting materials for producing these polymers as well as manifold molecular adaptations of the molecular parameters of the polymer to application requirements. This includes, for example, molar mass and its distribution, avoidance of the formation of false structures, obtaining and controlling stereoisomerism, etc.

The polymer is produced in a multistep process involving biotechnological and chemical process steps, which mainly comprises:

- hydrolyzing starch-containing substrates to glucose;
- fermenting the glucose to L-lactic acid;
- polycondensation to a low-molecular poly-L-lactic acid;
- cyclizing depolymerization to L,L-dilactide;
- ring-opening polymerization of the L,L-dilactide to poly-L-lactic acid;
- stabilizing and demonomerizing the polymer.

With high-molecular polyesters, a direct polycondensation of L-lactic acid is only possible under laboratory conditions by means of an azeotropic method in a solvent for the monomer and the polymer. Due to the position of the ring/chain equilibrium of linear and cyclic oligomers, technical methods have to use the described multistep process including low-molecular poly-L-lactic acids and L,L-dilactides as intermediate steps (see Scheme 1).

Scheme 1. Reaction scheme of poly-L-lactic acid synthesis from L-lactic acid

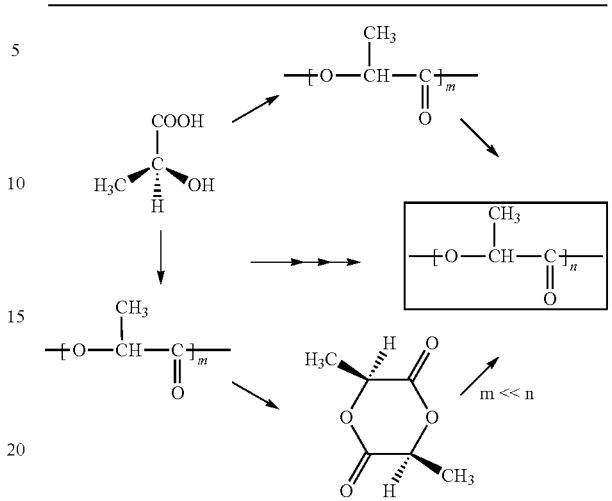

This multistep process for producing poly-L-lactic acid is described in numerous patents, particularly those to Cargill Inc. USA (see e.g. U.S. Pat. Nos. 6,277,951, 6,005,067, 5,357,035, 6,291,597, CA 2,128,509), Dainippon Ink & Chem. Japan (see e.g. U.S. Pat. Nos. 5,844,066, 5,616,657, 5,605,981, 5,403,897), Mitsui Toatsu Japan (see e.g. U.S. Pat. No. 5,194,473), Neste Oy Finland (WO 98/36008), Brussels Biotec (see e.g. GB 2,407,572, WO 98/02480, DE 69905016, U.S. Pat. No. 6,489,508, US 2004/0014991) or Shimadzu Japan (see e.g. U.S. Pat. Nos. 5,770,682, 5,866,677, JP 7206851).

Irrespective of technological and apparatus-related concepts in the patent specifications mentioned, obtaining a polymerizable L,L-dilactide is a main feature of the described methods. Chemical and chiral or stereochemical purity (with L,L-, D,D- and meso-dilactides) of dilactides that are formed from lactic acid produced by fermentation (L- and D-lactic acid) or a chemical process (D,L-lactic acid) is essential for the production of a high-molecular polylactic acid with appropriate morphological and thermal properties. D-lactide units in the poly-L-lactic acid, introduced by incomplete separation of D,D-dilactide or meso-dilactide during work-up of the L,L-dilactide, act despite their same chemical structure like comonomers and influence the tacticity of the macromolecule. This leads to changes in the morphology of the polymeric solid with the observed macroscopic changes in melting and softening behavior as well as in selected mechanical properties. Here, the morphological changes are a direct function of the content of D-lactide units in the polymer (regarding morphological and mechanical properties of PLA see e.g. D. W. Grijpma et al., Makromol. Chemie 195, 1649 (1994), G. Perego et al., J. Appl. Polymer Sci. 59, 37 (1996), G. Schmack et al., J. Appl. Polymer Sci. 73, 2785 (1999), R. E. Drumright et al., Adv. Mater 12 H 23, 1841 (2000), R. Auras et al., Macromol. Biosci. 4, 835 (2004)).

The stereoisomers of L,L-dilactide are to be viewed as "impurities" and have to be separated laboriously. The distribution of the stereoisomeric L,L-, D,D- and meso-dilactides during depolymerization of a poly-L-lactide with D-monomer portions in the chain can be calculated according to Equations (1a) to (1c) for a complete turnover and with p for the L-lactide content in the chain:

| L,L-dilactide: | $p^2$ | (1a) |
| meso-dilactide: | $2p(1-p)$ | (1b) |
| D,D-dilactide: | $(1-p)^2$ | (1c) |

While with D-portions under 10% (corresponding to p>0.9 for the L-monomer portion), the formation of D,D-dilactides is negligible, the amount of meso-dilactides formed within this range may considerably reduce the yield and complicate the work-up of the L-monomer.

The property rights claimed therefore mainly focus on techniques for the production and purification of the monomer including apparatuses used. The effectiveness and selectivity of cyclizing depolymerization of oligo-L-lactic acid and purification methods for raw lactides thus relate to the protection claimed in the above patent specifications in the same way. They mostly describe purification methods by distillation under vacuum (see e.g. U.S. Pat. No. 6,277,951), but GB 2,407,572 also describes a raw-lactide purification process for a more strongly contaminated dilactide including a laborious multistep melt crystallization process in combination with crystallization from a solution. In particular, meso-dilactides and L-lactic acid as well as linear oligomers of lactic acid have to be laboriously separated from raw lactides. Lactic acid and its linear oligomers are compounds containing OH and COOH groups and thus influence the ring-opening polymerization of L,L-dilactides by controlling the molar mass as a result of chain breakage. A meso-dilactide introduces D-lactide units into the macromolecule that constitute "defects" leading to morphological changes in the solid including, as is known, a reduction of crystallinity and an ensuing decrease of the melting point or solidity.

For cyclizing depolymerization, a low-molecular oligo-L-lactic acid is used, which is obtained by polyesterification of L-lactic acid in most of the published methods. In CA 2,128,509, a process variation is described where L-lactic acid alkyl ester is oligomerized by polytransesterification.

The polycondensation of L-lactic acid is a typical AB-type polycondensation reaction of a monomer (OH and COOH groups on a monomer) comprising the cleavage of $H_2O$ as low-molecular component and activation by an $A_{Ac}2$ mechanism. Corresponding to the reaction steps typical for $A_{Ac}2$ reactions, a primary addition of electrophilic catalysts, preferably protons, to the carbonyl group (COOH group of lactic acid, lactoyl ester end groups in the case of oligomeric or polymeric lactic acids) is followed by the addition of nucleophilic reaction partners (OH group of the lactic acid, OH groups of lactoyl ester end groups in the case of linear oligomers or polymers) to the carbonyl carbon and the elimination of the original substituents. In principle, cations or complexes of selected metals, as used for AA/BB-type polycondensations (reaction of diols with dicarboxylic acid), should also activate this polyesterification of lactic acid. In particular, manganese, calcium, antimony, titanium or tin are used in the form of oxides, alkoxides or acetates for the production of polyalkylene terephthalates (PET, PBT, PTT), the selection from this pool of metal-based catalysts being subject to limits strictly defined by the respective polyester and technology. For instance, polyethylene terephthalate (PET) has long been exclusively produced in the presence of Sb compounds ($Sb_2O_3$ or $Sb(ac)_3$), while for polybutylene therephthalate (PBT), titanium alkoxides are mainly used as catalysts. Titanium alkoxides with their high catalytic activity are not suitable for PET because they lack hydrolysis-stability in the direct esterification of therephthalic acid with ethylene glycol and because the resulting polymer turns yellow. Only recently PET may also be synthesized in the presence of special titanium compounds (DE 10337522). This patent specification claims complexes of titanium, zirconium and hafnium as catalysts for the production of aromatic-aliphatic polyesters of the AA/BB type. However, with polycondensation temperatures of 250° C. (PBT) and 280° C. (PET) and a largely anhydrous reaction system consisting of therephthalic acid and an alkanediol (ethylene glycol, butanediol), these catalysts are used under significantly different conditions compared to the polycondensation of lactic acid. In particular, the use of a 80-85% aqueous lactic acid and lowering of the process temperature by approx. 100° C. are to be mentioned.

Due to a parallel activation of ether formation, the inorganic ($H_2SO_4$) or organic acids ($RSO_3H$) normally used in preparative organic chemistry are unsuitable as catalysts of lactic acid polycondensation because these ethers could also cyclize in cyclizing depolymerization due to the thermodynamic preference of six-membered ring systems. These cyclic ethers would then constitute additional impurities in the dilactide that are difficult to separate and could interfere with ring-opening polymerization or negatively influence the molecular parameters of the end product.

Cyclizing depolymerization of oligo- or polylactic acid to dilactide is mainly based on the thermodynamic concepts of ring/chain equilibria of cyclic esters (lactones) and amides (lactames), as e.g. described in detail in H.-G. Elias: Makromoleküle, 6$^{th}$ ed., Weinheim: Wiley-VCH (2002). Contrary to an autocatalyzed polycondensation of lactic acid to a low-molecular polyester, all described methods use catalysts, preferably tin(II) salts and tin(II) oxide, for accelerating the cyclizing depolymerization of these oligo- or polylactic acids to dilactides. As with polycondensation, the activation of cyclizing depolymerization is achieved by the addition of electrophilic catalysts, followed by the addition of the terminal nucleophilic OH group of the polyester to the ester carbonyl carbon and elimination by cyclization. It is also possible to initially form intermediate macrocycles by means of this backbiting process (H. Kricheldorf et al., Macromol. Chem., Macromol. Symp. 32, 285 (1990)), which are then further cleaved to obtain dimeric cycles.

OBJECT OF THE INVENTION

The object of the invention is to provide an improved, economically efficient method for producing L,L-, D,D-, D,L- or meso-dilactides, comprising the polycondensation of an L-, D- or D,L-lactic acid to a polyester of a higher molecular weight of the L-, D- or D,L-lactic acid (polylactic acids) and the cyclizing depolymerization of the polylactic acids to dilactides.

DESCRIPTION OF THE INVENTION

According to the invention, this is achieved by producing polyesters of higher molecular weights of the L-, D- or D,L-lactic acids for a cyclizing depolymerization in the presence of hydrolysis-stable metal compounds as catalysts.

The catalysts are characterized by high stability so that with a batch-wise execution of the experiment that includes depolymerization after polymerization in the same reactor, repeated dosing of lactic acid is possible without the necessity of redosing the catalyst. Of course, the catalyst has to be replenished in a continuous method and when the polycondensate is transferred in a separate depolymerization reactor.

U.S. Pat. No. 6,277,951 states that in the case of higher molar masses, racemization in the form of the generation of meso-dilactides increases. Thus, the meso-dilactide content is approx. 5.3% when a starting oligomer with $M_n$=520 g/mol is used. An increase of the molar mass of the pre-polymer to 2,500 g/mol leads to a parallel increase of the meso-dilactide content in the distillate to approx. 11%. In addition, it is stated that cations generally increase the formation of meso-dilactides.

The analysis results of the cyclizing depolymerization of polylactic acids produced according to the inventive method are summarized in Tables 1 to 3. The effective rate constants of the depolymerization determined are very complex and are a result of the overlap of the chemical reactions taking place in the system with the mass transfer of the dilactide from the melt into the gas phase. The chemical reactions determining the dilactide formation rate are besides the actual depolymerization mainly the ring-opening polymerization, in accordance with the equilibrium character of the PLA formation, as well as the hydrolysis of the dilactide as side reaction. Considering this dependence on the system, Table 1 shows the relative rates for the selected experimental method.

TABLE 1

Effective rate constants of dilactide formation as dependent on the molar mass of the pre-polymer

| $M_n$ [g/mol] | Catalyst | Rel. process rate |
|---|---|---|
| 550 | − | 1.0 |
| 800 | + | 1.1 |
| 3500 | + | 3.8 |
| 6100 | + | 9.2 |
| 7500 | + | 12.0 |
| 10000 | + | 14.1 |

COOH group concentration and angle of rotation reflect the purity of a raw lactide, wherein the COOH group concentration is indicative of direct linear oligomers, preferably lactoyl lactic acid. They can be formed by ester-typical trans-esterification reactions with the involvement of the end groups as well as by hydrolysis of the dilactide. The optical activity, measured by means of the angle of rotation, is indicative of chemical as well as optical impurities of the dilactide.

TABLE 2

COOH concentration in a raw L,L-dilactide as dependent on the molar mass of the pre-polymer (depolymerization temperature: 200° C.)

| $M_n$ [g/mol] | [COOH] [mmol/g] |
|---|---|
| 550 | 1.20 |
| 800 | 0.75 |
| 3500 | 0.21 |
| 6100 | 0.13 |
| 7500 | 0.08 |
| 10000 | 0.06 |

TABLE 3

Angle of rotation of the raw L,L-dilactide as dependent on the molar mass of the pre-polymer (depolymerization temperature: 200° C.)

| $M_n$ [g/mol] | [α] [deg] |
|---|---|
| 550 | −235 |
| 800 | −247 |
| 3500 | −255 |
| 6100 | −257 |
| 7500 | −260 |
| 10000 | −260 |

In comparison, the rotation value of a pure L,L-dilactide is −282°. It is clearly shown that a higher molecular weight leads to a purer product.

In a further embodiment of the invention, polylactic acids can be produced by polycondensation of lactic acid or poly-transesterification of lactic acid esters. The catalysts used in the inventive method can also be used for activating poly-transesterification of lactic acid esters to polylactic acids according to Eq. (2).

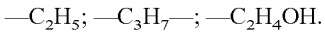 Eq. (2)

with R:
—$C_2H_5$; —$C_3H_7$—; —$C_2H_4OH$.

These catalysts also accelerate the polycondensation of lactic acid/lactic acid ester mixtures. Lactic acid esters constitute an alternative to classic methods for purifying lactic acids by membrane or precipitation processes. They can be separated from the raw lactic acid by distillation after trans-esterification with alkanoles.

In the method of the present invention, polylactic acids are polymerized in the presence of a hydrolysis-stable catalyst to molar masses between 800 g/mol and 10,000 g/mol, preferably 6,000 g/mol and 10,000 g/mol, more preferably 7,000 g/mol and 10,000 g/mol, most preferably between 8,000 g/mol and 10,000 g/mol. This increase of the molecular weight obtainable in polycondensation allows a depolymerization to purer products so that subsequent purification steps become less laborious or can even be omitted.

The hydrolysis-stable metal compounds are preferably selected from metal compounds of titanium, zirconium and tin, more preferably of titanium and zirconium. The use of these compounds makes it possible for the first time to produce polylactic acids of higher molecular weights with number-average molar masses of up to 10,000 g/mol and with high process rates by polycondensation at milder temperatures, which acids are then supplied to the depolymerization step. Contrary to an autocatalyzed polycondensation of L-, D- or D,L-lactic acids according to the state of the art, the catalyst concentration remains unchanged during the entire process in the case of an externally catalyzed polycondensation. The COOH group and thus the proton concentrations decrease rapidly with increasing molar masses because of a decrease of the end group concentration. Similarly, the rate quickly decreases with an increase of the turnover of COOH groups in these reactions autocatalyzed by COOH groups.

The use of tin(II) halides, tin(II) carboxylates or tin(II) oxides in the oligomerization of a lactic acid, which according to the state of the art are used as catalysts for ring-opening polymerization as well as cyclizing depolymerization in almost all published methods (see e.g. the US, GB and CA patent documents already mentioned), would take advantage of the independence of an externally catalyzed polycondensation from the end group concentration, however, being typical polymerization or depolymerization catalysts, they preferably accelerate the formation of dilactides and not of polymers, even at low average molar masses. Accordingly, in GB 2,407,572 the formation of dilactides starts at molar masses of 400 g/mol (range 400 to 2,000 g/mol) (process autocatalyzed by COOH of L-lactic acid: L-lactide in the precondensate 97.6%, externally catalyzed: L-content in the dilactide 87.8%). The generation of dilactides by using a pre-polymer of very low molecular weight leads to a very high content of impurities in the raw lactide that later on interfere with the polymerization, which impurities have to be separated by means of laborious and repeated crystallization steps. These impurities are caused by water that is, because of the low molar masses, still formed in high amounts by parallel polycondensation processes during depolymerization, and it can hydrolyze dilactides already formed in the melt or in the distillates to lactoyl lactic acid or lactic acid. According to Eq. (3), (n−1) moles of water are formed from n moles of lactic acid during polycondensation. Considering the connection between number-average polymerization degree and reaction progress degree in Eq. (4a) and (4b), this means, for example, that 900 g (10 mol) of an anhydrous lactic acid result in 162 g of water, correspondingly 81 g in the case of dimerization, or approx. 146 g when the linear decamer with $M_n$=738 g/mol is produced. When a linear oligomer with $M_n$=3,000 g/mol (corresponding to $P_n$=41.6) is produced, approx. 158 g of water have to be removed from the system for the same amount of lactic acid. Even after transition of $P_n$=10 to $P_n$=41.6, 12 g of water are still available for dilactide hydrolysis. This corresponds to a hydrolysis potential of 0.67 mol/mol when the dilactide is separated and worked up.

$$n\text{CH}_3\text{CH(OH)COOH} \longleftrightarrow [\text{—OCH(CH}_3)\text{CO—}]_n + (n-1)\text{H}_2\text{O} \quad \text{Eq. 3}$$

$$P_n = 1/(1-p) \quad \text{Eq. 4a}$$

$$p = 1 - 1/P_n \quad \text{Eq. 4b}$$

The high activity of the inventive catalysts allows for the use of a very low amount of $5 \cdot 10^{-5}$ to $1 \cdot 10^{-2}$ mol of catalyst metal/mol of monomer unit. By means of catalyst structure and catalyst concentration, the polycondensation rate as well as the maximum molar mass obtainable in the melt can be controlled. For comparable process conditions, there is an almost linear relation between obtainable molar masses and catalyst concentrations (Table 4).

TABLE 4

$M_n$ values of L-lactic acid polycondensates as dependent on catalyst concentration

| Cat. conc. * $10^4$ [mol/mol] | $M_n$ [g/mol] |
| --- | --- |
| Without | 550 |
| 0.1 | 800 |
| 0.75 | 1600 |
| 1.0 | 2300 |
| 3.5 | 3400 |
| 6.0 | 4800 |
| 8.5 | 7500 |
| 10.5 | 10000 |

Polycondensation conditions: T: 180° C.; p: 1.6 kPa; t: 4 h

Contrary to the state of the art, it was found that the Ti and Zr catalysts used in the inventive method do not only accelerate polycondensation and lead to higher molar masses of the poly-L-lactic acids produced by polycondensation, but that these poly-L-lactic acids with higher molar masses also depolymerize more quickly and lead to a purer raw lactide. The higher molar mass results in reduced end group concentrations and thus also in a reduction of parallel and subsequent reactions of the depolymerization. The most important parallel reaction of cyclizing depolymerization under the selected conditions (high temperature, vacuum) is the polycondensation of OH and COOH end groups, in the course of which water is formed. This water can then, in a subsequent step, hydrolyze previously formed dilactides in the reaction melt as well as in the vapor (Scheme 2). Both reactions reduce the process rate of dilactide formation.

Scheme 2. Reaction scheme of dilactide hydrolysis

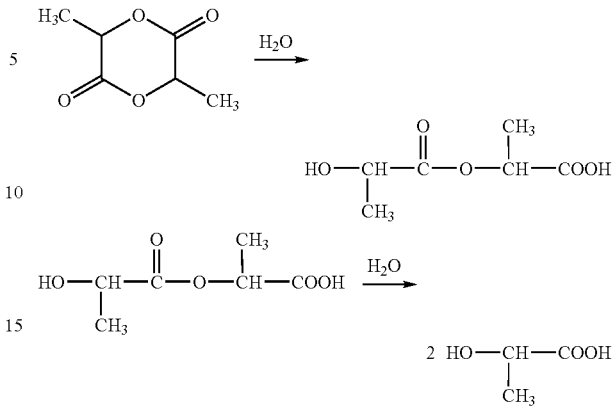

Preferably, the hydrolysis-stable catalysts for the polycondensation of lactic acids or for the polytransesterification of lactic acid esters used in the inventive method are complexes of titanium or zirconium of the following structure:

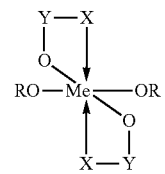

wherein:

Me = Ti, Zr:
R = ——H, -Alkyl, -Aryl, ——PO(OR')$_2$, ——HPOOR', ——SO$_2$R';
X = >O, >S; and
Y = >CH——, >C<, >P<.

It is thus proposed that the production of low-molecular poly-L-lactic acid is conducted in the presence of an esterification or transesterification catalyst that is selected from metal chelates of subgroup IV of the periodic table of elements with the general structure shown in Scheme 3.

Scheme 3. General structure of chelates of metals of subgroup IV proposed for the polycondensation of L-, D- and D,L-lactic acids and esters of these lactic acids

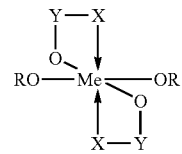

Herein, Me, R, X and Y are defined as above.
Chelating components preferably used for the structures shown in Scheme 3 are:
  acetylacetonates
  alkali and ammonium lactates
  phosphoric acid and pyrophosphoric acid esters
  phosphorous acid esters
  ethanolamines and ethanoldiamines.

With dihydroxy-bis-(ammoniumlactato)-titanate (Tyzor LA, DuPont) (Scheme 4, center), isopropyl-tri-(dioctylphosphato)-titanate (KR 12, Kenrich Petrochemicals), isopropyl-dioctylphosphatodi-(octylpyrophosphato)-titanate (KR 38 S, Kenrich Petrochemicals) (Scheme 4, right) and diisopropyl-bis-(acetylacetonato)-titanate (Scheme 4, left), various of such chelate complexes of titanium are available, this selection not limiting the catalytically active compounds but solely illustrating the structural diversity available.

Scheme 4. Examples of catalytically active chelate complexes of titanium

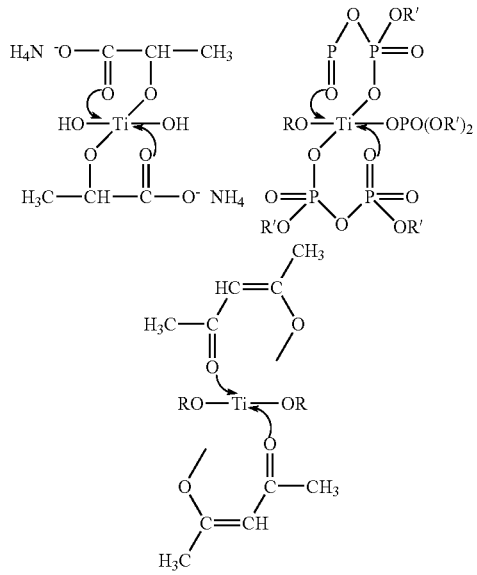

Chelate structures of the type shown in Scheme 3 are coordinatively saturated so that they have, contrary to titanium and zirconium alkoxides, sufficient hydrolytic and thermal stability and are thus not damaged or deactivated under the technical process conditions of the polycondensation of L-, D- or D,L-lactic acids or their esters.

The titanium and zirconium compounds used for accelerating the polycondensation of lactic acids in the inventive method are commercially available from DuPont or Kenrich Petrochemicals.

In a preferred embodiment of the invention, the complexes of titanium or zirconium used for catalysis can thus have further functionalities through the selected ligands that can contribute to further improving catalysis and thus to higher yields.

In another preferred embodiment of the invention, the above catalysts can also be used in combination with technologically or structurally appropriate cocatalysts for producing polyesters of L-, D- or D,L-lactic acids of higher molecular weights, as long as the effect of the invention is not hindered. For example, the inventive catalysts can be used in combination with known esterification and transesterification catalysts without loss of their catalytic effectiveness. Suitable technologically or applicationally appropriate system components are, for example, tin(II) halides, tin(II) carboxylates and tin(IV) alkoxides as well as zinc and antimony compounds. Depending on the hydrolytic stability of these cocatalysts, these catalyst combinations may also be used for directly polycondensing lactic acids with higher water contents, wherein the additional effect of a reduction of the volatility of lactic acid during dehydration and polycondensation can be observed.

In one embodiment of the invention, the raw dilactides can be further purified by means of conventional methods of rectification, melt crystallization or solution crystallization. Thus, equipment generally known and available in laboratories and factories may also be used for the inventive method. No new investment is necessary.

According to the state of the art, the depolymerization of polylactic acids produced by polycondensation has been conducted in the presence of tin(II) chloride or tin(II) octonoate at temperatures of 180 to 240° C. under a vacuum of 133 Pa and with the separation of the dilactide formed via a heated column. Also according to the state of the art, the raw lactide can be purified by distillation or by crystallization.

In a second aspect, the invention thus relates to L,L-, D,D-, D,L- and meso-dilactides produced according to the inventive method with the advantageous properties mentioned above, particularly high stereoselectivity.

In a third aspect, the invention relates, as mentioned above, to the use of such an L,L-, D,D-, D,L- or meso-dilactide for producing polyesters of L-, D- or D,L-lactic acid, respectively, preferably polyesters with number-average molar masses $M_n$ of more than 125,000 g/mol and molecular polydispersities $M_w/M_n$ between 1.6 and 3.0. The production of such polyesters of lactic acid with high molecular weights and uniform molar mass distributions is easily possible because the dilactides obtained according to the inventive method have a high stereoselectivity.

The dilactides produced according to the invention were used for polymerization experiments including discontinuous and continuous methods in order to assess their suitability for polymer production. For the discontinuous polymerization experiment, a glass apparatus with a screwed blade stirrer was used. For the continuous polymerization experiment, a twin-screw extruder with a screw design specifically adjusted to this bulk polymerization was used. In the presence of tin(II) octonoate and depending on the polymerization conditions (temperature, cocatalyst addition, stabilization) and the method (discontinuously in a stirred reactor or horizontal kneader, continuously in a twin-screw extruder), polymers with number-average molar masses in the range of 40,000 g/mol<$M_n$<175,000 g/mol at molecular polydispersities of 1.5<$M_w/M_n$<3.0 were synthesized.

The invention will be described in the following examples, which are provided for illustration only and not for limitation.

EXAMPLES

Example 1

Polycondensation, Comparative Example 1060 g of a 85% L-lactic acid (experimental product of the applicant) are completely dehydrated in a glass apparatus equipped with a stirrer, an external heater and a temperature-controlled Vigreux column in vacuum at 155° C. within 2 h, the vacuum being controlled so that no lactic acid is carried off via the distillate. After the dehydration phase, the temperature is increased to 185° C., and polycondensation is conducted for 6 h at 13 kPa. The yield, molar mass and [COOH] content of the polycondensation product are determined.

Yield: 725 g
$M_n$: 550 g/mol
[COOH]: 1.9 mmol/g

Example 2

Polycondensation, According to the Invention

In analogy to Example 1, 1060 g of a 85% L-lactic acid (experimental product of the applicant) are completely dehydrated in a glass apparatus equipped with a stirrer, an external heater and a temperature-controlled Vigreux column in vacuum at 155° C. within 2 h, the vacuum being controlled so that no lactic acid is carried off via the distillate. After the dehydration phase, the temperature is increased to 185° C., and polycondensation is conducted for 4 h at 13 kPa with the addition of $10^{-4}$ mol/mol of dihydroxy-bis-(ammoniumlactato)-titanium (Tyzor® LA, DuPont) (0.6 g of a 50% solution). In analogy to Example 1, the yield, molar mass and [COOH] content of the polycondensation product are determined.
Yield: 730 g
$M_n$: 2,300 g/mol
[COOH]: 0.4 mmol/g

Example 3

Polycondensation, According to the Invention

In analogy to Example 2, 1060 g of a 85% L-lactic acid (experimental product of the applicant) are completely dehydrated in a glass apparatus equipped with a stirrer, an external heater and a temperature-controlled Vigreux column in vacuum at 155° C. within 2 h, the vacuum being controlled so that no lactic acid is carried off via the distillate. After the dehydration phase, the temperature is increased to 200° C., and polycondensation is conducted for 4 h at 13 kPa with the addition of $3*10^{-4}$ mol/mol of isopropyl-tri-(dioctylphosphato)-titanate (KR®12, KENRICH Petrochemicals) (3.2 g).
Yield: 730 g
$M_n$: 3,600 g/mol
[COOH]: 0.3 mmol/g

Example 4

Polycondensation, According to the Invention)

In a liquid-heated 25 l laboratory stirred tank equipped with an anchor agitator, a jacket heater, a bottom valve and a temperature-controlled column as well as with jacket interior and exterior temperature detection, 15 kg of a 65% L-lactic acid are dehydrated in vacuum at 120 to 160° C. (vapor-controlled temperature program) and subsequently polycondensed for 4 h at 190° C. in the presence of $3.0*10^{-4}$ mol/mol of dihydroxy-bis-(ammoniumlactato)-titanium (22 g of a 50% solution).
Yield: 10 kg
$M_n$: 3,400 g/mol
[COOH]: 0.4 mmol/g

Example 5

Polycondensation, According to the Invention

In analogy to Example 4, in a liquid-heated 25 l laboratory stirred tank equipped with an anchor agitator, a jacket heater, a bottom valve and a temperature-controlled column as well as with jacket interior and exterior temperature detection, 15 kg of a 65% L-lactic acid are dehydrated in vacuum at 120 to 160° C. (vapor-controlled temperature program) and subsequently polycondensed for 4 h at 190° C. in the presence of a catalyst combination consisting of $2.0*10^{-4}$ mol/mol of dihydroxy-bis-(ammoniumlactato)-titanium and $2*10^{-4}$ mol/mol of $SnCl_2$.
Yield: 10 kg
$M_n$: 4,800 g/mol
[COOH]: 0.2 mmol/g

Example 6

Polycondensation, According to the Invention

In analogy to Example 2, 1060 g of a 85% L-lactic acid (experimental product of the applicant) are dehydrated and polycondensed for 3 h with the addition of a catalyst combination consisting of $2*10^{-4}$ mol/mol of isopropyl-tri-(dioctylpyrophosphato)-titanate (KR®38, KENRICH Petrochemicals) (2.6 g) and $3*10^{-4}$ mol/mol of $Sn(C_2O_4)$. In analogy to Example 1, the yield, molar mass and [COOH] content of the polycondensation product are determined.
Yield: 730 g
$M_n$: 6,100 g/mol
[COOH]: 0.13 mmol/g

Example 7

Polycondensation, According to the Invention 900 g of an anhydrous L-lactic acid (experimental product of the applicant) are polycondensed for 5 h in a glass apparatus equipped with a stirrer, an external heater and a temperature-controlled Vigreux column in vacuum at temperatures of 150-210° C. in the presence of $5.5*10^{-4}$ mol/mol of isopropyl-tri-(dioctylphosphato)-titanate (KR®12, KENRICH Petrochemicals) (3.2 g) and $5*10^{-4}$ mol/mol of $SnCl_2$. The temperature and vacuum program is adjusted to not carry off any lactic acid via the distillate. The product is completely dehydrated in vacuum at 155° C. within 2 h. The final vacuum chosen is 13 kPa. By analogy with Example 1, the yield, molar mass and [COOH] content of the polycondensation product are determined.
Yield: 730 g
$M_n$: 10,000 g/mol
[COOH]: 0.06 mmol/g

Example 8

Polycondensation, According to the Invention

In analogy to Example 2, 920 g of a commercially available D,L-lactic acid are polycondensed with the addition of $2*10^{-4}$ mol/mol of dihydroxy-bis-(ammoniumlactato)-titanium and worked up. In analogy to Example 1, the yield, molar mass and [COOH] content of the polycondensation product are determined.
Yield: 700 g
$M_n$: 2,600 g/mol
[COOH]: 0.3 mmol/g

Example 9

Polytransesterification, According to the Invention 1180 g of ethyl-L-lactate (experimental product of the applicant) are polycondensed in a glass apparatus equipped with a stirrer, an external heater and a temperature-controlled Vigreux column at 200° C. in the presence of $3*10^{-4}$ mol/mol of dihydroxy-bis-(ammoniumlactato)-titanium. Cleaved off ethanol is removed via the column and may be directly reused for the esterification of L-lactic acid. For a complete separation of ethyl ester groups, the reaction is continued under vacuum after removal of the main part of ethanol formed.

Yield: 700 g
$M_n$: 3,500 g/mol
[COOH]: 0.1 mmol/g

Example 10

Cyclizing Depolymerization 1000 g of a poly-L-lactic acid produced according to Examples 2 to 8 are heated in a glass apparatus equipped with a stirrer, an external heater and a temperature-controlled packed column with a likewise temperature-controlled cooler under a vacuum of 1.3-2.0 kPa in the presence of a tin(II) catalyst. If one of the described tin(II)-containing catalyst combinations is used in the polycondensation, no further catalyst addition is necessary. If one of the tin(II) containing catalyst combinations described is used in polycondensation, no further catalyst addition is necessary. If only the preferred titanium or zirconium chelates alone are used as catalyst for the production of pre-polymers, $2*10^{-4}$ mol/mol of $SnCl_2$, $Sn^0$ or $Sn(C_2O_2)$ are additionally added as depolymerization catalyst to the oligomer melt. Depending on the selected depolymerization rate, the reaction mixture is then heated to 185-220° C., and L,L-dilactide formed is removed via the column, while the cooler temperature is held at 100° C. to avoid crystallization.

Depending on the substrate and the selected depolymerization conditions, raw L,L-dilactides with the carboxyl group contents and angles of rotation [α] shown in Tables 3 and 4 are obtained.

For fine purification, the raw lactides are distilled in vacuum or are recrystallized from acetic ethyl ester in the presence of $CaCO_3$ as acid acceptor in order to separate residual lactic acid, linear oligomers and residual water. The L,L-dilactide for bulk polymerization thus purified by distillation or crystallization is characterized by:

$T_m$: 96 to 97° C.
[α]: −268 to −270°
[COOH]: 8 μmol/g

D,L-dilactide purified by distillation or crystallization has the following data:

$T_m$: 126 to 127° C.
[COOH]: 10 μmol/g

Example 11

Ring-opening Polymerization, Discontinuous, Cylindrical Glass Container 36 g of an L,L-dilactide produced and purified according to Example 9 and carefully dried are melted in a cylindrical glass reactor equipped with a wall-to-wall screwed blade stirrer (propeller agitator) under inert gas in a tempering bath. The propeller agitator made of glass and reaching down to the bottom axially intermixes the melt. The agitator is operated with a rotational speed of 100 $min^{-1}$. After reaching the required temperature, $7.5*10^{-5}$ mol/mol of $Sn(oct)_2$ in the form of a 0.1% solution in toluene are added. For determining the polymerization progress, samples of the melt can be taken via a lateral access to determine their monomer turnovers and molar masses. The determination of the turnover was conducted gravimetrically by reprecipitating polylactic acids from chloroform as solvent and a methanol/diethyl ether mixture as precipitating agent. The molar masses were determined by means of GPC in $CH_2Cl_2$. For calibration, polystyrene standards were used.

After a polymerization time of 20 min, the following was determined:

Monomer turnover: U=96%
Molar mass: $M_n$=60,000 g/mol
Molecular polydispersity: $M_n/M_w$=2.1

Example 12

Ring-opening Polymerization in a Twin-Screw Extruder

For bulk polymerization of an L,L-dilactide by means of a reactive extrusion process, a corotating and closely intermeshing twin-screw extruder with interior temperature and torque control was used. The twin-screw extruder used has an (L/D) ratio of 35 and screws with a modular design so that the screw configuration regarding transport, kneading and baffle elements can be optimally adjusted to process conditions and end product parameters.

1000 g of an L,L-dilactide in the form of a crystalline powder, dried in a vacuum-drying cabinet at 40° C. over $P_4O_{10}$, was intensively mixed with a solution of tin(II) octonoate in toluene in a laboratory tumble mixer, after which the toluene was stripped in vacuum. The catalyst concentrations were $3.0*10^{-4}$, $2.0*10^{-4}$ and $1.5*10^{-4}$ mol/mol and corresponded to a tin content of 247, 165 and 123 ppm, respectively.

Dosing of the lactide/catalyst mixture was performed by means of volumetric dosing via dosing screws.

Turnover: 94%
$M_n$: 112,000 g/mol
$M_w$: 239,000 g/mol

The above description clearly shows that by using hydrolysis-stable metal compounds according to the invention as catalysts, it was possible to produce polylactic acids with high molecular weights and low COOH contents, which were subsequently depolymerized to very pure dilactides. Thus, an efficient method has been provided for producing dilactides that can, because of their high purity, be used for the production of polyesters of lactic acid with little or no further purification.

The invention claimed is:

1. A method for the production of L,L-, D,D-, D,L- and meso-dilactides, comprising the steps of (i) polycondensation and/or polytransesterification of an L-, D- or D,L-lactic acid or of esters thereof to polyesters of higher molecular weights of the L-, D- and D,L-lactic acid and (ii) cyclizing depolymerization of said polyesters to dilactides, wherein the polyesters of higher molecular weights of the L-, D- and D,L-lactic acids are produced in step (i) in the presence of a hydrolysis-stable complex of titanium or zirconium of the following structure, as a catalyst:

$$\begin{array}{c} Y-X \\ | \\ O \\ \diagdown \\ RO-Me-OR \\ \diagup \\ O \\ | \\ X-Y \end{array}$$

wherein:
Me is Ti or Zr;
R is —H, -alkyl, -aryl, —PO(OR')$_2$, —HPOOR' or —SO$_2$R';
X is >O or >S; and
Y is >CH—, >C< or >P<
and wherein the chelating components are:
acetylacetonates,
alkali and ammonium lactates,
phosphoric acid and pyrophosphoric acid esters,
phosphorous acid esters, or
ethanolamines and ethanoldiamines, and that during polycondensation and polytransesterification in step (i), the lactic acids are polymerized to molar masses between 6,000 g/mol and 10,000 g/mol.

2. The method according to claim 1 wherein the complexes of titanium or zirconium have further functionalities on the selected ligands.

3. The method according to claim 1, wherein the catalyst is present alone or in combination with a technologically and/or structurally appropriate cocatalyst.

4. The method according to claim 1, further comprising purifying the dilactides by rectification, melt crystallization or solution crystallization.

5. The method according to claim 1, wherein during step (i), the lactic acids are polymerized to molar masses between 7,000 g/mol and 10,000 g/mol.

6. The method according to claim 5, wherein during step (1), the lactic acids are polymerized to molar masses between 8,000 g/mol and 10,000 g/mol.

* * * * *